(12) United States Patent
Sang et al.

(10) Patent No.: US 7,259,291 B2
(45) Date of Patent: Aug. 21, 2007

(54) ENUCLEATION OF AVIAN EGGS BY GAMMA IRRADIATION

(75) Inventors: Helen Sang, Midlothian (GB); Adrian Sherman, Midlothian (GB)

(73) Assignee: Viragen Incorporated, Plantation, FL (US)

( * ) Notice: Subject to any disclaimer, the term of this patent is extended or adjusted under 35 U.S.C. 154(b) by 292 days.

(21) Appl. No.: 10/498,286

(22) PCT Filed: Dec. 13, 2002

(86) PCT No.: PCT/GB02/05660

§ 371 (c)(1),
(2), (4) Date: Jun. 4, 2004

(87) PCT Pub. No.: WO03/049537

PCT Pub. Date: Jun. 19, 2003

(65) Prior Publication Data

US 2005/0015825 A1  Jan. 20, 2005

(30) Foreign Application Priority Data

Dec. 13, 2001 (GB) .................................. 0129811.6

(51) Int. Cl.
C12N 15/00 (2006.01)
(52) U.S. Cl. .......................................... 800/24; 435/447
(58) Field of Classification Search .................. 800/24, 800/8, 13; 435/447
See application file for complete search history.

(56) References Cited

U.S. PATENT DOCUMENTS

2006/0010510 A1 * 1/2006 Christmann .................. 800/19

OTHER PUBLICATIONS

Cibelli et al. Cloned Transgenic Calves produced from Nonquiescent Fetal Fibroblasts. Science May 22, 1998, vol. 280, pp. 1256-1258.*

Parsons, James E. et al., "Production of androgenetic rainbow trout", *The Journal of Heredity*, 76:177-181 (1985).

Straume, T et al., "Neutron RBEs and the Radiosensitive Target for Mouse Immature and Oocyte Killing", *Radiation Research*, 111:47-57 (1987).

Tatham, Brendan G. et al., "Enucleation by Centrifugation of In Vitro-Matured Bovine Oocytes for Use in Nuclear Transfer", *Biology of Reproduction*, 53:1088-1094 (1995).

Nour, M.S. Mohamed et al., "Preparation of Young Preactivated Oocytes with High Enucleation Efficiency for Bovine Nuclear Transfer", *Theriogenology*, 51:661-666 (1999).

Dominko, T. et al., "Dynamic Imaging of the Metaphase II Spindle and Maternal Chromosomes in Bovine Oocytes: Implications for Enucleation Efficiency Verification, Avoidance of Parthenogenesis, and Successful Embryogenesis", *Biology of Reproduction*, 62:150-154 (2000).

Babiak, I. et al., "Androgenesis in rainbow trout using cryopreserved spermatozoa: the effect of processing and biological factors", *Theriogenology*, 57:1229-1249 (2002).

Carsience, et al., "Germline chimeric chickens from dispersed donor blastodermal cells and compromised recipient embryos", *Development* 117, 669-675 (1993).

* cited by examiner

*Primary Examiner*—Deborah Crouch
(74) *Attorney, Agent, or Firm*—Drinker Biddle & Reath LLP; Daniel A. Monaco

(57) ABSTRACT

A method of enucleating an egg by exposing the egg to gamma irradiation. The dose of gamma irradiation used is sufficiently high to halt development of the egg or embryo derived therefrom directed by the nucleus of the irradiated egg, but sufficiently low to enable development of the egg or embryo directed by a nucleus transferred into the enucleated egg.

7 Claims, 1 Drawing Sheet

ENUCLEATION OF AVIAN EGGS BY GAMMA IRRADIATION

Figure 1:
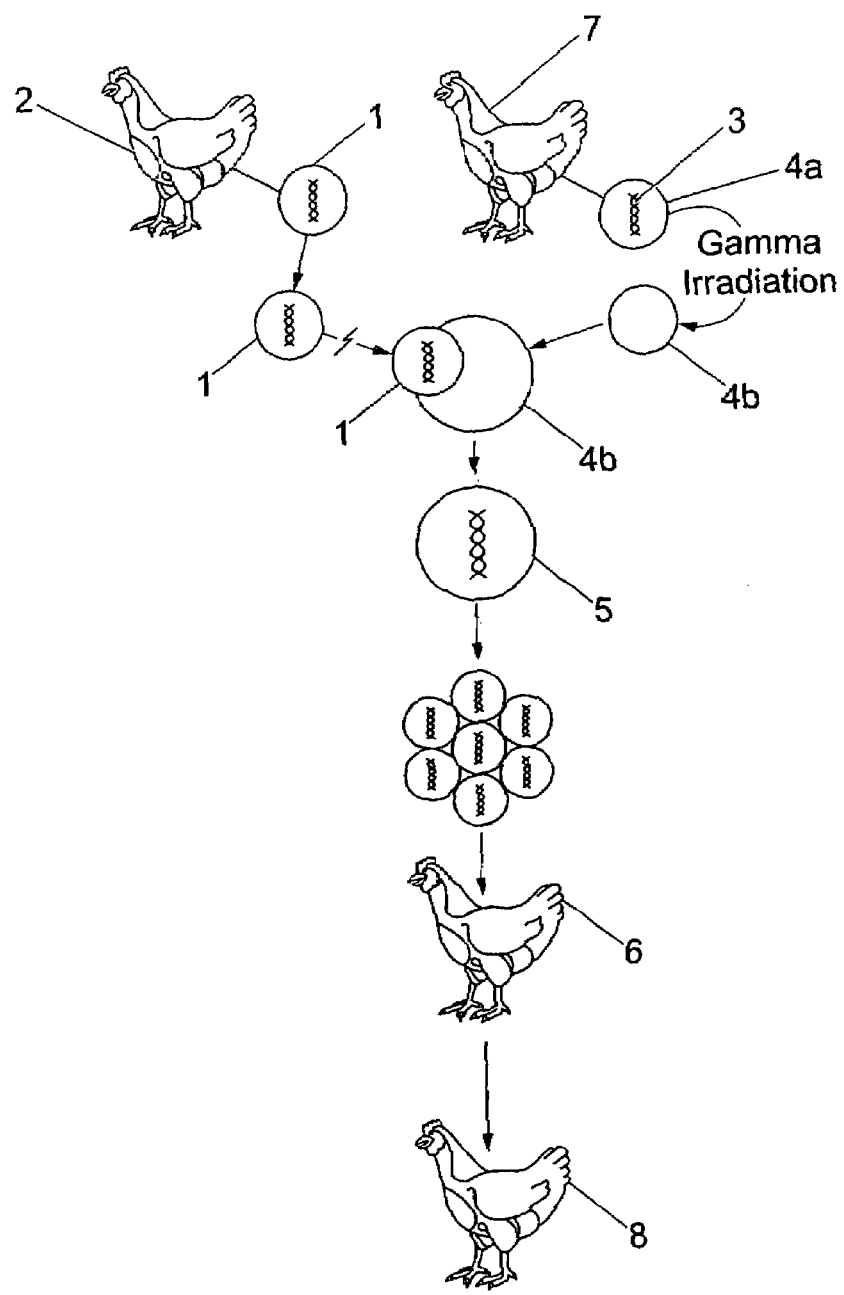

The present invention relates to a method of enucleating eggs, in particular eggs for use, for example, as recipient cells for nuclear transfer techniques.

The first demonstration of embryo cloning by means of nuclear transfer was made in 1952 (Briggs and King, Proc. Natl. Acad., Sci. USA 38 455-461 (1952). Since then, nuclear transfer techniques have been demonstrated in a number of species, culminating in the production of "Dolly", the sheep (Campbell et al, 1996, Nature 380 64-66).

The reconstruction of embryos by the transfer of a donor nucleus to an enucleated oocyte or one cell zygote allows the production of genetically identical individuals. This has clear advantages for both research (i.e. as biological controls) and also in commercial applications (i.e. multiplication of genetically valuable livestock, uniformity of meat products). Nuclear transfer also forms the basis for development of an efficient method of genetic modification of livestock species. If the donor cell has been genetically modified the animal that develops after nuclear transfer will contain that genetic modification (McCreath K J, Howcroft J, Campbell K H, Colman A, Schnieke A E, Kind A J. (2000) Nature 405 1004-1005).

Nuclear transfer or transplantation techniques involve the transfer of an intact nucleus from one cell to another which has had its nuclear DNA removed or destroyed. In particular, the process involves the introduction of a donor nucleus into the cytoplasm of a recipient egg or oocyte, which thus receives the genetic material from a donor nucleus and has the potential of developing into an embryo that will develop into a viable adult animal.

In order to successfully produce an animal by nuclear transfer techniques, it is necessary to transfer the nucleus of the donor cell to an enucleated recipient egg. All successful nuclear transfer methods, in amphibians, mammals and fish, have required enucleation of the recipient egg prior to introduction of the donor nucleus which replaces the egg nucleus and directs development. Enucleation involves the removal or inactivation of the nucleus of the recipient egg.

The recipient egg may either be an unfertilised egg or a recently fertilised zygote stage egg. If the egg has not been fertilised it will contain the female pronucleus which must be removed or inactivated. If the egg has been fertilised it will contain the female pronucleus and a male pronucleus or multiple male pronuclei derived from sperm after fertilisation. Each of these must be removed or inactivated prior to replacement with a donor nucleus.

Enucleation of a recipient egg is therefore a major limiting step in nuclear transfer methods. To date, a number of methods have been used.

In amphibia such as *Xenopus*, enucleation is usually carried out by means of ultraviolet irradiation, which inactivates the nucleus by damaging the DNA (Gurdon, 1986 J. Cell. Sci. Suppl. 4 287-318). Another method of enucleation, which has been used with amphibian eggs such as those of leopard frogs is manual manipulation using a needle.

In mammals, enucleation is usually carried out by the physical removal of an egg nucleus using a micropipette (see for example, Campbell et al, 1996, Nature 380 pp64-66; Wakayama et al, 1998, 369-374).

In fish, physical enucleation has been used to prepare recipient eggs for nuclear transfer in zebrafish (Lee et al, Nature Biotechnol. 2002 August; 20(8):795-9). The enucleation of unfertilised medaka fish oocytes by X-rays has been reported (Wakamatsu et al, PNAS (2001) 98 pp1071-1076).

However, although successful enucleation has been achieved in a number of species, problems persist with the known methods. For example, physical enucleation is technically very demanding and success rates are low; UV irradiation is associated with heat generation, which may cause unacceptable damage to the cell; and X ray enucleation requires high doses of X rays which similarly may cause unacceptable damage to the cell.

The enucleation step thus remains a major limiting step in nuclear transfer experiments and can be very difficult to achieve. This problem is particularly important in avian cells, which are especially difficult to successfully enucleate due to the unique structure of avian eggs. The female pronucleus is positioned in the germinal disc, the white spot of approximately 2 mm diameter that lies on the surface of the yolk.

The avian egg is composed largely of the yolk and is very large and fragile compared to the eggs of other animals. It therefore cannot be manipulated with the ease that amphibian, mammalian or fish eggs can be handled. Problems arise when attempting to use a method of physical enucleation in avian eggs as the pronucleus/pronuclei in an avian egg cannot easily be visualised and is/are thus difficult to remove manually. UV irradiation of avian eggs is similarly unsatisfactory. Evaluation of the use of UV radiation in a hen's egg shows that the dose of UV required to stop development of a fertilised egg generates so much heat that the egg is damaged. X ray irradiation is not suitable as the high doses required and the duration of exposure required is likely to cause unacceptable damage to the cell.

Therefore, it can be seen that it would be beneficial to provide an alternative efficient method of enucleation, particularly a method that can be used to efficiently enucleate avian eggs.

It is a further object of the present invention to provide a method of enucleating eggs without causing the eggs to be damaged in such a way that they can no longer be used for nuclear transfer methods.

A yet further object of the present invention is to provide a simple and quick method of enucleation.

SUMMARY OF THE INVENTION

The present inventors have surprisingly found that gamma radiation may be used to efficiently enucleate eggs, in particular avian eggs, such that development directed by the nucleus of the irradiated eggs is halted but such that development directed by a donor nucleus transferred into the irradiated egg may proceed.

According to a first aspect of the present invention, there is provided a method of enucleating an egg by exposing the egg to gamma irradiation.

Preferably the dose of gamma irradiation used is sufficiently high to halt development of the egg or embryo derived therefrom directed by the nucleus of the irradiated egg, but sufficiently low to enable development of the egg or embryo directed by a nucleus transferred into the enucleated egg.

Therefore, the dose is such that the irradiated nucleus is incapable of directing any development. Thus, any development directed by the nucleus of the irradiated egg prior to the irradiation is halted and any development directed by the nucleus of the irradiated egg is prevented. Any subsequent development must be directed by a nucleus transferred into the enucleated egg.

The method of the invention may be used with any animal egg, for example, mammalian, amphibian, avian, reptilian or insect eggs. In preferred embodiments the egg is an avian egg.

The egg for use in the methods of the invention may be an unfertilised egg or a recently fertilised zygote stage egg.

The egg may be exposed to gamma radiation for any time period long enough to deliver sufficient radiation to halt development directed by the nucleus of the irradiated egg but short enough to enable the egg to be used as a recipient egg for nuclear transfer techniques. If the egg is not fertilised the dose will be sufficient to stop development of an equivalent fertilised egg. For example, the dose will be short enough to enable development of the egg or embryo derived therefrom to develop directed by a donor nucleus transferred into the egg.

The duration of exposure to radiation, the dose per minute and the total dose applied to the egg is dependent on a number of factors, for example the size and type of egg.

In preferred embodiments of the present invention, the egg is exposed to gamma radiation for a period of time in the range 1 minute to 10 minutes, for example, 2 to 5 minutes, preferably 2 to 4 minutes.

In another preferred embodiment of the invention, the egg is exposed to gamma radiation for a period in the range 1 to 3 minutes.

The dose of radiation per minute is preferably in the range 2 to 25 Gy per minute irradiation dose, for example, 2 to 20, 2 to 15, 2 to 12, 2 to 10, 2 to 8, 2 to 6, 5 to 25, 10 to 25, 15 to 25, 5 to 10, 5 to 15 or 10 to 15 Gy per minute.

In one preferred embodiment, the egg is exposed to a 15 Gy per 1 minute to a 25 Gy per 1 minute irradiation dose, for example a 18 6 Gy per 1 minute irradiation dose. Preferably, in this embodiment, the radiation doses are as measured using the RX20/53M Irradiator (Gravatom Industries Ltd. (Gosport, Hampshire)) at the Institute of Cell, Animal and Population Biology, University of Edinburgh.

In another preferred embodiment, the egg is exposed to a 2 Gy per 1 minute to 12 Gy per 1 minute irradiation dose.

The total dose of gamma irradiation used is preferably greater than 7 Gy, for example, greater than 8 Gy, preferably greater than 9 Gy, more preferably greater than 10 Gy, yet more preferably greater than 11 Gy, most preferably greater than 12 Gy.

In a particularly preferred embodiment, the total dose of radiation is between 12 and 14 Gy, for example 12.8 Gy.

Preferably the egg is exposed to between 10 and 62.5 Gy irradiation dose in total, for example, between 10 and 50, 10 and 40, 10 and 30, 20 and 62.5, 20 and 50, 20 and 40, 20 and 30, 30 and 62.5, 30 and 50, 30 and 40, 40 and 62.5, 40 and 50 and 50 and 62.5 Gy.

In one preferred embodiment, the egg is exposed to between 37 Gy and 62.5 Gy total irradiation dose, more preferably to between 42.5 Gy and 47.5 Gy irradiation dose in total, even more preferably to a total dose in the range 44-45 Gy. Preferably, in this embodiment, the radiation doses are as measured using the RX20/53M Irradiator (Gravatom Industries Ltd. (Gosport, Hampshire)) at the Institute of Cell, Animal and Population Biology, University of Edinburgh.

In another preferred embodiment, the egg is exposed to between 6 and 18 Gy dose in total. In a particularly preferred embodiment, the total dose is about 12 Gy, for example 12.8 Gy.

Most preferably irradiation is carried out in the nuclear transfer procedure prior to, most preferably immediately prior to the injection of a donor nucleus.

The eggs enucleated according to the first aspect of the invention and their use in nuclear transfer techniques, for example to reconstitute an animal embryo, are also provided by the invention.

Accordingly, in a second aspect of the present invention there is provided a method of generating an animal embryo, wherein the method comprises enucleating an egg according to the method of the first aspect of the invention, transferring a diploid nucleus from a donor cell into the enucleated egg and allowing the resultant embryo to develop.

The donor nucleus may be obtained from any suitable cell, which may be fully or partially differentiated cells or undifferentiated cells. Cells may be cultured in vitro or abstracted ex vivo. The only limitation is that the donor cells have normal DNA content and be karyotypically normal. A useful source of cells is described in WO 96/07732.

In order to produce transgenic embryos and animals using the method of the invention, the donor nucleus may be genetically modified using any method known in the art, for example micro-injection, mass transformation or transfection e.g. electroporation, viral transfection or lipofection.

In order to effect nuclear transfer, any suitable method known in the art, for example, cell fusion or microinjection (Ritchie and Campbell, J. Reproduction and Fertility Abstract Series No. 15, p60) may be used.

Further details of methods useful in the generation of embryos using nuclear transfer techniques can be found in WO 96/07732 and WO 97/07668, the contents of which are herein incorporated by reference.

According to a third aspect of the present invention, there is provided a viable reconstituted animal embryo prepared by the method of the second aspect of the invention.

According to a fourth aspect of the invention there is provided a method of preparing an animal comprising the steps (a) generating an embryo according to the method of the second aspect of the invention and (b) allowing an animal to develop from the reconstituted embryo.

The method may comprise further step (c) breeding from an animal formed in step (b).

Animals produced by the method of the invention form a further aspect of the present invention.

The embryo may be allowed to develop to term in vivo or in vitro. Where the embryo is mammalian, the embryo must be transferred to a recipient female to develop to term. However, development to blastocyst stage may take place in vitro before transfer to a recipient surrogate mother to carry the embryo to term. However, if it is a fish or an amphibian, eg a frog then the egg may be kept in a simple solution in vitro in which eggs normally develop.

In preferred embodiments of the invention, the egg is an avian egg. As described above, the differences in the eggs of avians and other vertebrates means that development of the embryo takes place in a hard shell egg.

In preferred embodiments of this aspect of the present invention, wherein the egg is an avian egg, the embryo may be transferred to a recipient oviduct of a female avian to be laid in a hard shell.

In a preferred embodiment, an avian embryo may be allowed to develop to term in vitro or in a host shell by a modification of the technique described in WO 90/13626. According to this aspect of the invention, an egg is removed from a female bird, enucleated according to the method of the first aspect of the invention, fused with a donor nucleus to generate an embryo and allowed to develop to hatching within a host shell.

The basic method of this aspect of the invention may involve:
Removal of an unfertilised egg or a newly-fertilised egg from a hen
Transfer of the egg into a prepared host shell
Enucleation according to the first aspect of the invention
Introduction of a donor cell or nucleus into the germinal disc
Addition of medium such as egg white, e.g. collected from fresh egg, to the injected egg in the shell
Covering the egg e.g. with a plastic lid and incubation in an incubator e.g. in 5% carbon dioxide for 24 hours at 41° C.
Addition of more medium, sealing the egg with e.g. cling film and incubation for e.g. 3 days at 37.5° C.
Optionally, transfer of the contents of this egg to a larger egg, to leave an airspace over the developing embryo
Incubation until hatch.

The invention further provides an animal generated using a method of the invention.

The present invention will now be illustrated, by way of example only, with reference to the following Figure, in which:

FIG. 1 shows a diagrammatic overview of a typical nuclear transfer procedure.

EXAMPLE 1

The method of nuclear transfer (as shown in FIG. 1) typically comprises of the following steps:

Firstly a cell 1 is extracted and cultured from the donor animal 2 and the nucleus 3 is removed from a recipient egg cell 4a of another animal 7, then the cell extracted from the first animal is fused into the enucleated egg cell 4b to provide a fused cell 5 which can be cultured and then implanted into a surrogate mother 6. The implanted egg may give rise to a cloned animal 8.

For the nuclear transfer step to be successful, the enucleation of the recipient egg cell is very important and is a limiting step in the nuclear transfer methods currently available.

In this example, gamma irradiation is used to enucleate an avian egg. The gamma irradiation source used was the RX20/53M Irradiator (Gravatom Industries Ltd. (Gosport, Hampshire)) at the Institute of Cell, Animal and Population Biology at the University of Edinburgh, United Kingdom.

In order to stop development of embryos in new laid hens' eggs, the eggs were exposed to gamma irradiation for 2.5 mins. In order to determine the approximate dose required to inhibit development of fertilised zygotes, the zygotes stage eggs from laying hens were removed and then irradiated using a gamma irradiation source to provide an irradiation dose of approximately 45 Gy over 2.5 minutes.

Preliminary results showed that a dose of 1 to 3 minutes at a rate of 15-25 Gy per 1 minute (preferably 18 Gy per 1 minute) was sufficient to stop the development of embryos in new laid eggs. Over the 1 to 3 minutes a total dose of 37 Gy was found to be useful with 44 Gy or 45 Gy also being useful. All doses referred to in this example were as estimated using the RX20/53M Irradiator (Gravatom Industries Ltd. (Gosport, Hampshire)) at the Institute of Cell, Animal and Population Biology at the University of Edinburgh, United Kingdom.

In order to determine the approximate dose necessary to inhibit development of fertilised zygotes, the zygotes stage eggs were removed from fertile laying hens and transported in a heated incubator to the gamma irradiation source. The eggs were then irradiated through a range of different times and then cultured to enable the subsequent developmental potential of the embryos to be estimated. Control eggs were also carried through the same procedure, but not irradiated. The results of one of the experiments are shown in Table 1.

The table shows that manipulation and transport of eggs impaired the development of the control embryos, as it is normally expected that 60% of the eggs will develop normally. In this case, only 30% developed normally. Further studies suggest however that removing the need to transport eggs to an irradiation source would avoid the problems with the control eggs.

TABLE 1

Gamma irradiation of magnum recovered zygotes

| Treatment Culture number | Distance to Isthmus (cm) | Age/stage at death (up to d7) |
|---|---|---|
| CONTROL | | |
| 2 | 16 | Twins 3d |
| 4 | 12 | + |
| 6 | 9 | 5d |
| 13 | 14 | + |
| 16 | 18 | Lb |
| 17 | 31 | Lb |
| 2.5 MIN IRRADIATION | | |
| 3 | 19 | Nd |
| 5 | 16 | Nd |
| 7 | 10 | Nd |
| 8 | 15 | Sb |
| 9 | 13 | Sb |
| 18 | 22 | Sb |
| 3 MIN IRRADIATION | | |
| 1 | 11 | Nd |
| 10 | 23 | Nd |
| 11 | 13 | Lb |
| 12 | 20 | 4d |
| 14 | 18 | Sb |
| 15 | 15 | Nd |

Notes

Zygotes harvested and set up in host shells

Transported to Institute of Cell, Animal and Population Biology, University of Edinburgh from Roslin Institute in portable incubator (39° C.)

Cultured for up to 7 days:

Nd=No development

Sb=small blastoderm

Lb=large blastoderm 3 d, 5 d, 7 d=day of developmental stage

Normal development=7 d

The data shown in the table suggests that gamma irradiation is completely inhibiting or severely impairing development of the irradiated embryos.

EXAMPLE 2

Accurate Determination of Gamma Irradiation Dose

Methods

Calibration of the RX20/53M Irradiator irradiation source used in Example 1 demonstrated that at low doses, this machine overestimated the dose of gamma radiation being delivered to a target. In order to more accurately estimate the minimum dose of radiation required to inhibit development of embryos directed by irradiated nuclei and yet enable development directed by donor nuclei transferred to the irradiated egg, the irradiation experiments were repeated using a Nordion International Inc. Gammacell 3000 Elan machine at the Blood Transfusion Service in Edinburgh.

The preparation of eggs prior to irradiation and treatment of eggs after irradiation was identical to the treatment of the eggs used in the experiment described in Example 1.

Briefly, magnum recovered eggs from fertile hens were placed in 'Phase I' culture host-shells (Fertilisation to blastoderm formation—see WO 90/13626) with a single layer of gauze over the yolk to prevent drying of the germinal disc and placed in a high humidity 5% $CO_2$/42° C. incubator.

Eggs to be irradiated were transferred to a humidified heated (37° C.) transporter box and taken to the irradiator. The transport incubator at 37° C. contained water to keep humidity high with 30 secs moderate $CO_2$ stream introduced into the travel incubator before transport to the source in Edinburgh and foam was placed over the eggs.

Eggs were removed two at a time and placed in the irradiator canister.

The eggs were divided into control and treatment groups and the treatment groups irradiated. The eggs of example 2 were divided into four groups—treatment group 1 (total dose of radiation 6.4 Gy), control group 1 (total dose of radiation 0 Gy), treatment group 2 (total dose of radiation 12.8 Gy), and control group 2 (total dose of radiation 0 Gy).

After irradiation (of the treatment group eggs) the eggs were returned to the box. When all eggs were treated the box was transported to the laboratory where they were returned to the 5% CO2/42° C. incubator.

EXAMPLE 2

Results

As described above, the eggs of example 2 were divided into four groups—treatment group 1 (total dose of radiation 6.4 Gy), control group 1(total dose of radiation 0 Gy), treatment group 2 (total dose of radiation 12.8 Gy), and control group 2 (total dose of radiation 0 Gy).

Development of the zygotes was assessed at 3 days after irradiation, using the classification of Hamburger and Hamilton (1951) J. Morphol. 88, 49-92.

Results are shown in Tables 2 and 3.

TABLE 2

1 min (6.4Gy) irradiation of zygotes:

| Treatment | Est. Dose (Gy) | Dev. at 3d (stage) | |
|---|---|---|---|
| Controls | 0 | 17 | |
|  |  | 16 | |
|  |  | Nd | |
|  |  | 15 | |
|  |  | 17 | |
|  |  | 16 | |
|  |  | 15 | |
|  |  | 16 | |
| 1 min | 6.4 | SB | 6 mm |
| " | " | SB | 4 mm |
| " | " | nd | |
| " | " | 15 sm | 16 mm |
| " | " | SB odd | 6 mm |
| " | " | 15 Av irreg | |
| " | " | 15 sm | 15 mm |

Development after 3 days would normally be to stage 17 (Hamburger and Hamilton, 1951).
SB: Small blastoderm
LB: Large blastoderm
Nd: no development
15, 16, 17: stages according to classification of Hamburger and Hamilton (1951)
sm: small
av irreg: average stage 15 but irregular shape
nfd: no further development
Normal development achieved with control zygotes.

3 irradiated zygotes developed embryos but were retarded to st.15 and small or irregular shaped.

TABLE 3

2 min (total dose 12.8Gy) irradiation of zygotes:

| Treatment | Est. Dose (Gy) | Dev. at 3d (stage) |
|---|---|---|
| Controls | 0 | LB noE |
|  |  | 16 |
|  |  | LB mishapen |
|  |  | 16 |
|  |  | 15 |
|  |  | 16 |
|  |  | Twins 2xst.6 |
| 2 min | 12.8 | nfd |
| " | " | nfd |
| " | " | nfd |
| " | " | nfd |
| " | " | nfd |
| " | " | nfd |
| " | " | nfd |

Only 4/7 controls developed normally
2 min irradiation resulted in no further development of the disc (~3 mm laid egg blastoderm) some showing vacuoles.

EXAMPLE 3

Generation of Embryos by Nuclear Transfer

Recipient eggs are enucleated using the method described in Example 2.

Briefly, magnum recovered eggs from fertile hens are placed in 'Phase I' culture host-shells with a single layer of gauze over the yolk to prevent drying of the germinal disc and placed in a high humidity 5% $CO_2$/42° C. incubator.

Eggs to be irradiated are transferred to a humidified heated (37° C.) transporter box and taken to the irradiator. The transport incubator at 37° C. contains water to keep humidity high with 30 secs moderate $CO_2$ stream introduced into the travel incubator before transport to the source and foam was placed over the eggs.

Eggs are removed and placed in the irradiator canister and irradiated with a total dose of gamma readiation of 12.8 Gy over a period of two minutes. After irradiation the eggs are microinjected with cells as described below.

2 µl of a cell suspension is pipetted onto a microscope slide so that a droplet is formed. A glass micro-capillary (tip bevelled to a 300 angle with a diameter of 25-30 µm) held by a Research Instruments micro-capillary holder is lowered into the droplet at a shallow angle such that the tip is just touching the slide surface. Cells are loaded into the micro-capillary by negative air pressure controlled by a hand-operated syringe. 1-10 cells are loaded in a minimum volume (<0.5 nl) by taking up cell suspension and ejecting excess solution as cells rise towards the meniscus.

The slide is removed and the microscope focus adjusted to give a working distance beneath the objective lens suitable for the egg to be injected. The egg with the gauze layer removed from the yolk is placed under the microscope and the germinal disc located. Magnification is adjusted such that the entire disc (approx. 3 mm) filled the field of view. The micro-capillary was lowered into place above the centre of the disc at an angle of −45° and controlled by the micro-manipulator so as to just puncture the vitelline membrane and penetrate approximately 50 µm into the germinal disc cytoplasm.

The magnification is then increased to view the site of injection so that the depth of entry can be assessed. The micro-capillary is marked with drawing ink at a distance of 50 µm from the tip in order to judge this depth. The cell suspension is ejected as slowly as possible using the hand-operated air-syringe. After injection the needle is withdrawn, a fresh gauze layer applied, the petri-dish lid re-placed and the egg returned to the 5% $CO_2$/42° C. incubator for incubation overnight.

The injected eggs are transferred into "Phase II" culture (embryonic morphogenesis—see WO 90/13626) at a time 24 hours after the egg was removed from the donor hen and the eggs are monitored.

It can be seen that this method has a number of advantages over the current methods of enucleation. For example, it will now be possible to enucleate avian eggs without damaging the eggs in such a manner that would prevent their use in nuclear transfer experiments. It is also an appropriate method for use in other animals, if required.

All documents referred to in this specification are herein incorporated by reference. Various modifications and variations to the described embodiments of the inventions will be apparent to those skilled in the art without departing from the scope and spirit of the invention. Indeed, various modifications of the described modes of carrying out the invention which are obvious to those skilled in the art are intended to be covered by the present invention. For example, dosage rates, amounts and the time over which a dose may be given may be altered depending on requirements.

The invention claimed is:

1. A method of enucleating an avian egg, wherein the egg is exposed to gamma radiation, wherein the dose of gamma radiation is sufficiently high to halt development of the egg or an embryo derived therefrom directed by the nucleus of the irradiated egg, but sufficiently low to enable development of the egg or embryo directed by a nucleus transferred into the enucleated egg, wherein the total dose of gamma irradiation is greater than 7 Gy.

2. The method according to claim 1, wherein the egg is exposed to gamma radiation for a period of time between 1 and 3 minutes.

3. The method according to claim 1, wherein the total dose of gamma radiation is greater than 10 Gy.

4. The method according to claim 1, wherein the total dose of gamma radiation is greater than 12 Gy.

5. The method according to claim 1, wherein the total dose of gamma radiation is in the range of 12 Gy to 14 Gy.

6. The method according to claim 1, wherein the wherein the total dose of gamma radiation is in the range 37 Gy to 62.5 Gy.

7. The method according to claim 1, wherein the total dose of gamma radiation is in the range 44.5 Gy to 47.5 Gy.

* * * * *